(12) United States Patent
Guillermin et al.

(10) Patent No.: US 9,827,206 B2
(45) Date of Patent: Nov. 28, 2017

(54) METHOD FOR PRODUCING AN ADHESIVE MATERIAL FOR MEDICAL APPLICATION

(71) Applicant: ZODIAC COATING, Plaisir (FR)

(72) Inventors: Melanie Guillermin, Charvieu Chavagneux (FR); Jean-Roger Guillo, Serezin de la Tour (FR); Jean-Francois Lecoeuvre, Sorbiers (FR)

(73) Assignee: ZODIAC COATING, Plaisir (FR)

( * ) Notice: Subject to any disclaimer, the term of this patent is extended or adjusted under 35 U.S.C. 154(b) by 0 days.

(21) Appl. No.: 14/917,334

(22) PCT Filed: Sep. 24, 2013

(86) PCT No.: PCT/FR2013/052234
§ 371 (c)(1),
(2) Date: Mar. 8, 2016

(87) PCT Pub. No.: WO2015/044532
PCT Pub. Date: Apr. 2, 2015

(65) Prior Publication Data
US 2016/0220504 A1 Aug. 4, 2016

(51) Int. Cl.
| | | |
|---|---|---|
| *A61K 9/70* | (2006.01) | |
| *A61L 15/58* | (2006.01) | |
| *A61L 24/04* | (2006.01) | |
| *A61K 9/00* | (2006.01) | |
| *B05D 3/14* | (2006.01) | |
| *B29C 43/24* | (2006.01) | |

(52) U.S. Cl.
CPC .............. *A61K 9/70* (2013.01); *A61K 9/0048* (2013.01); *A61L 15/58* (2013.01); *A61L 24/046* (2013.01); *B05D 3/148* (2013.01); *B29C 43/24* (2013.01); *A61L 2420/02* (2013.01)

(58) Field of Classification Search
CPC ......... A61K 9/70; A61K 9/0048; A61L 15/58; A61L 24/046; A61L 2420/02; B05D 3/148; B29C 43/24
See application file for complete search history.

(56) References Cited

U.S. PATENT DOCUMENTS

| | | | | |
|---|---|---|---|---|
| 5,840,419 A | * | 11/1998 | Alder | B32B 27/18 428/304.4 |
| 5,965,226 A | * | 10/1999 | Muschelewicz | B32B 7/12 428/220 |
| 2006/0188706 A1 | * | 8/2006 | Kobayashi | B32B 7/12 428/317.1 |
| 2007/0202245 A1 | | 8/2007 | Gantner | |
| 2010/0255205 A1 | * | 10/2010 | Cray | C08K 5/541 427/386 |
| 2012/0208015 A1 | * | 8/2012 | Takahira | B32B 7/06 428/355 N |
| 2013/0053746 A1 | | 2/2013 | Roland | |
| 2013/0053806 A1 | | 2/2013 | Guillo | |

FOREIGN PATENT DOCUMENTS

| | | |
|---|---|---|
| EP | 2561844 A1 | 8/2012 |
| EP | 2561896 A1 | 2/2013 |
| FR | 2971971 A1 | 8/2012 |
| WO | 2005102403 A1 | 11/2005 |

OTHER PUBLICATIONS

Soft Skin Adhesive Gels and Liners: New Formulating Options for Tailored Solutions.

* cited by examiner

*Primary Examiner* — Sean M Basquill
(74) *Attorney, Agent, or Firm* — Gerald E. Hespos; Michael J. Porco; Matthew T. Hespos

(57) ABSTRACT

A method is provided for producing an adhesive material (1) for a medical application such as a dressing. The method includes at least one step for coating a first surface (2*b*) of any substrate (4), called receiving substrate, using a layer of previously coated silicone on an anti-adherent liner (3). The silicone layer is an adhesive gel (2). The method further includes, prior to the coating step, a corona treatment step for the surface of the adhesive silicone gel that is intended to coat the receiving substrate (4).

15 Claims, 3 Drawing Sheets

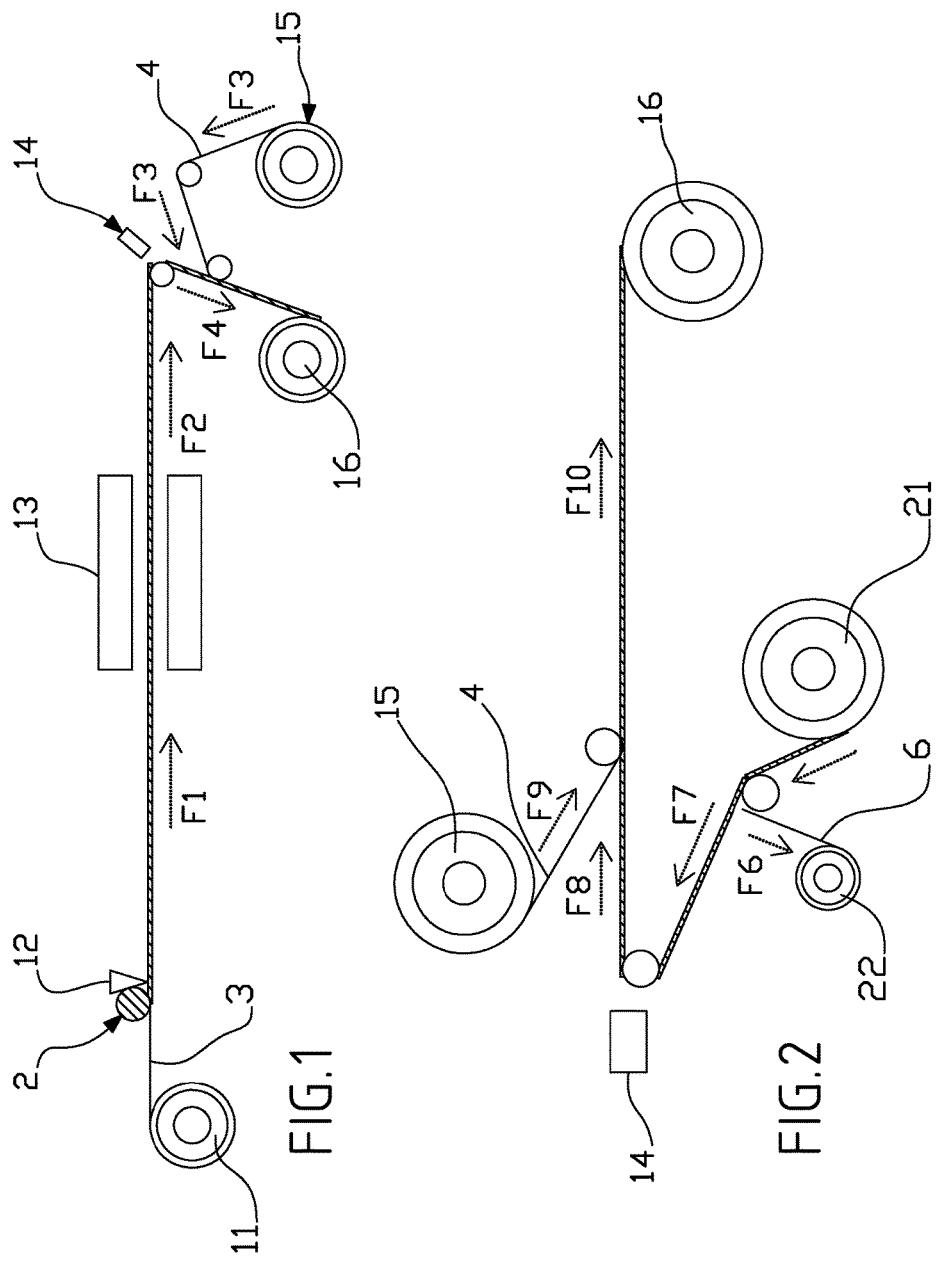

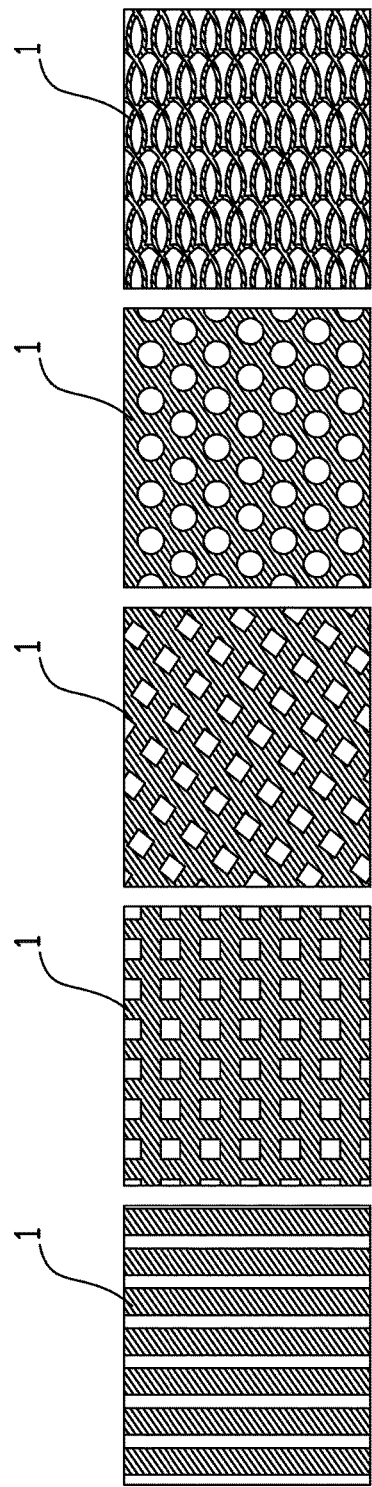
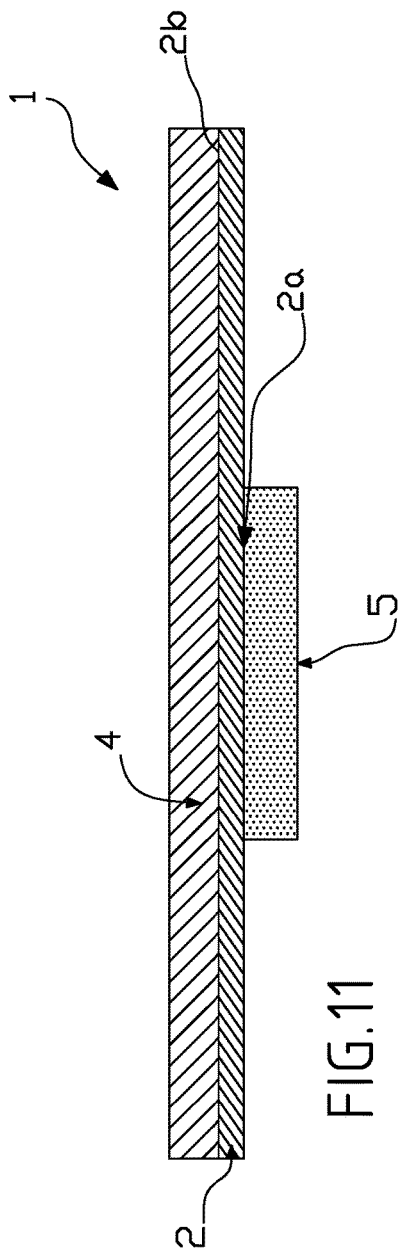
FIG.10 FIG.9 FIG.8 FIG.7 FIG.6
FIG.11

METHOD FOR PRODUCING AN ADHESIVE MATERIAL FOR MEDICAL APPLICATION

BACKGROUND

1. Field of the Invention

The present invention relates to a method for producing an adhesive material for medical applications, such as a dressing, and the material thus produced.

2. Description of the Related Art

There are currently different types of adhesive materials used to treat wounds (dressing components, protective adhesive films) and/or to use for maintaining compresses or medical devices (adhesive tapes, patches) designed for atraumatic contact with healthy skin and the wound.

Typically, such adhesive materials are obtained by different methods for depositing an adhesive on a receiving substrate.

Thus, for example known is a method for direct coating of the adhesive on the receiving substrate, followed by heat treatment of the adhesive (drying or cross-linking) and the placement of a protector (liner) on the adhesive face of the obtained material. Typically, the receiving substrate may be subject to coating with an adhesion primer or a corona treatment intended to favor the adhesion between the substrate and the adhesive.

However, this method may only be applied to substrates:
that are thermally compatible (no melting, softening or shrinkage), and
that have a low porosity opposing the crossing of silicone through the substrate during the coating.

This method often requires a prior, therefore costly, step for depositing an adhesion primer layer. As a result, this method is very limiting in terms of materials that can be produced and may have an excess production cost.

According to one known alternative embodiment, the adhesive is coated onto a film treated with an anti-adherent for the adhesive, then a lining operation is followed by calendaring of the receiving substrate on the adhesive before performing a heat treatment of the assembly (drying or cross-linking).

Nevertheless, this method requires receiving substrates:
that are thermally compatible (no melting, softening and/or shrinkage) with going through the cross-linking step of the silicone,
having a limited porosity and/or capillarity opposing the crossing and/or absorption of the adhesive through and/or by the receiving substrate during the time between the lining of the substrate on the adhesive in liquid state and the cross-linking of the adhesive, and
having a roughness or a fibrous surface allowing anchoring of the piece when a prior step for depositing a primer must be avoided.

This method often requires a prior, therefore costly, step for depositing an adhesion primer layer because the fusion between the silicone and the substrate may not be sufficient for the application, even with corona treatment of the substrate before coating.

As a result, this method is less limited in terms of materials that can be produced than the previous one, but also has an excess production cost.

According to a final embodiment, the adhesive is coated on a film treated with an anti-adherent for that adhesive, the adhesive is heat treated (drying or cross-linking), then a lining operation is done, followed by calendaring of the receiving substrate on the adhesive face. As a general rule, the receiving substrate is subject to a corona treatment intended to favor adhesion between the substrate and the adhesive.

This method should make it possible to open up possibilities for substrates intended for heat-sensitive uses (subject to melting, softening and/or shrinkage) and porous supports, since these substrates are applied on the adhesive without the substrates going through a cross-linking furnace on a still-liquid adhesive.

However, given the very low surface energy of silicone adhesives, such a method is applicable (or applicable in a very limited manner to certain substrates) because the adhesion force between the substrate and the silicone in cross-linked state is very weak, even if the substrate has undergone a prior corona treatment.

As a result, the obtained products:
for the large majority, are not industrially feasible: the adhesion between the silicone adhesive and the release process liner is greater than the adhesion between the silicone adhesive and the receiving substrate, which implies that the transfer of the adhesive mass is not occurring; and
can, in some cases, be industrially possible to produce, but have prohibitive weaknesses if the adhesion between the silicone adhesive and the patient's skin is greater than the adhesion between the silicone adhesive and the receiving substrate, which implies a malfunction of the medical device and/or unacceptable adhesive residues on the patient's skin.

Furthermore, in the general industrial field, and more particularly in the dressing and medical device industry, insufficient adhesion between a given adhesive and a material to be glued can be strengthened by corona treatment of the material to be glued.

Thus, for example, when a compress is deposited on a dressing having a base of a support coated with acrylic adhesive, better holding of the compress (whether dry or filled with water) is obtained via corona treatment of the face of the compress intended for gluing.

This works very well for acrylic adhesive and a large number of materials to be assembled or glued. However, this is not the case for a silicone adhesive for which a corona treatment applied to the materials to be assembled or glued does not yield satisfactory results due to the low surface energy of said silicone adhesive.

For example, in the case of an absorbent dressing compress, a low adhesion will be obtained when the compress is saturated with aqueous exudates from the wound. Silicone being hydrophobic by nature, there will no longer be any adhesion between the compress and the adhesive. It will then be difficult to remove the dressing because the layers of the dressing will separate from one another.

Thus, all of the known and previously described methods and materials have limitations.

One aim of the present invention is therefore to resolve the aforementioned problems, using an easy-to-implement and inexpensive solution that is optimized in terms of effectiveness, reliability, durability and quality of the obtained result.

SUMMARY

Thus, the present invention relates to a method for producing an adhesive material for a medical application such as a dressing, comprising at least one step for coating a first surface of any substrate, called receiving substrate, using a layer of previously coated silicone on an anti-adherent liner, characterized in that, the silicone layer being an adhesive gel, the method includes, prior to the coating step, a corona treatment step for the surface of the adhesive silicone gel that is intended to coat the receiving substrate.

The innovation lies in the application of the corona treatment applied directly on a silicone gel adhesive so as to reinforce the adhesion thereof on various substrates to produce the materials obtained by transferring the adhesive intended for medical applications.

According to preferred embodiments, the device according to the present invention comprises at least one of the following features:
- the silicone gel is cross-linked before the corona treatment;
- the step for coating the receiving substrate with the adhesive silicone gel is carried out in line with the coating in a single step;
- the step for coating the receiving substrate with the adhesive silicone gel is carried out separately from the coating through an additional step;
- the step for coating the receiving substrate with the adhesive silicone gel is performed by continuous solid surface coating;
- the adhesive silicone gel coating is done discontinuously so as to generate localized zones with no gel;
- the receiving substrate of the adhesive silicone gel is made up of a film of synthetic materials;
- the receiving substrate of the adhesive silicone gel is made up of a woven or knit textile from natural and/or synthetic fibers or fiber combinations;
- the receiving substrate of the adhesive silicone gel is made up of a nonwoven textile from natural and/or synthetic fibers or fiber combinations, obtained using the method applicable to its composition, for example dry or wet;
- the receiving substrate of the adhesive silicone gel is made up of a water-absorbent or draining foam serving to absorb or drain the exudates of a wound;
- the receiving substrate of the adhesive silicone gel is made up of a mechanical damping foam serving to protect against impacts, pressure and/or friction;
- the receiving substrate of the adhesive silicone gel is made up of a three-dimensional knit textile from natural and/or synthetic fibers or fiber combinations, having mechanical damping properties to protect against impacts, pressure and/or friction;
- the film of synthetic material, with a woven or knit textile, or the nonwoven textile, or the water-absorbent foam, or the mechanical damping foam, or the three-dimensional knit textile is associated with different functional layers and/or includes functional additives such as water absorption agents or disinfecting agents; and
- the adhesive silicone gel is dyed using pigments compatible with the anticipated medical application and the composition of said adhesive silicone gel.

The invention also relates to an adhesive material for medical applications, for example for producing dressings, in particular obtained using the method as previously described, to that end including a receiving substrate whereof one surface is coated with a layer of silicone previously coated onto an anti-adherent liner, characterized in that the silicone layer is a cross-linked silicone gel having undergone a corona treatment on the surface intended to coat the receiving substrate.

The invention will now be described in more detail in reference to specific embodiments provided as an illustration only and shown in the appended figures.

BRIEF DESCRIPTION OF THE DRAWINGS

FIGS. 1 and 2 are diagrams illustrating two methods for producing the material according to the present invention.

FIG. 6 is a front view of FIG. 5.

FIGS. 7 to 10 are alternative embodiments of FIG. 6.

FIG. 11 is a final alternative embodiment of FIG. 4.

DETAILED DESCRIPTION

Figure 4:
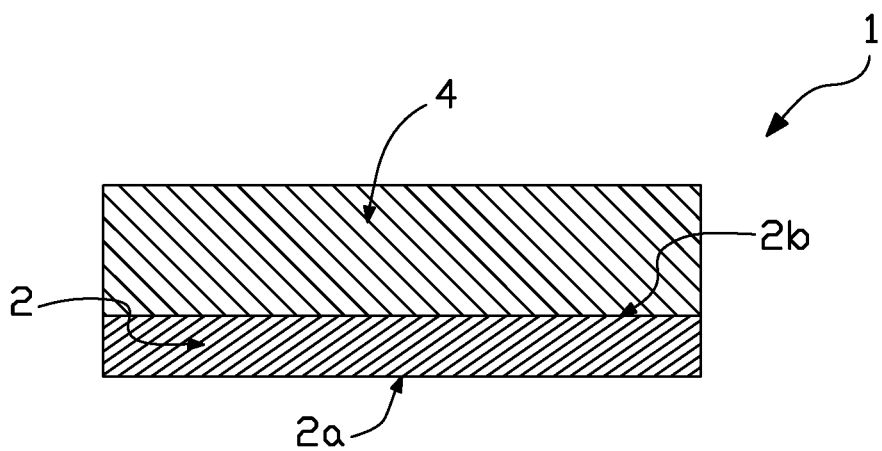

FIG. 1 shows a first embodiment of an adhesive material for medical applications 1, such as a dressing, like that for example illustrated in FIG. 4.

First, adhesive silicone gel 2 is coated onto an anti-adherent process liner 3 made from a material compatible with silicone, for example PET, wound around a spool 11. To that end, a transverse applicator 12 (for example a scraper, transfer cylinders, a flat extruder die or cord deposition nozzles) makes it possible to spread the adhesive silicone gel 2 on the anti-adherent process liner 3. This operation takes place continuously, the liner/silicone gel assembly progressing along arrow F1.

Figure 3:
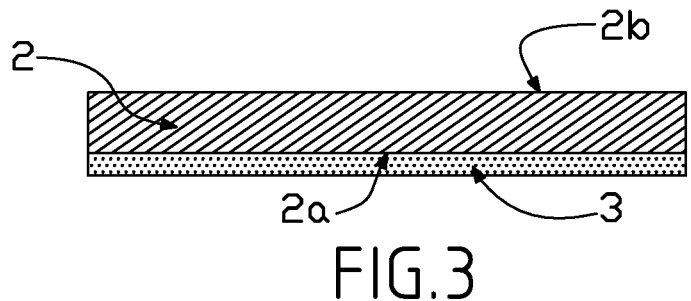
FIGS. 3 and 4 are sectional views illustrating two steps of the production of the materials.

In a second step, the anti-adherent process liner 3 coated with the layer of adhesive silicone gel 3 goes through a furnace 13, in which the layer of adhesive silicone gel 2 is cross-linked on the anti-adherent process liner 3. The liner/cross-linked silicone gel assembly (see FIG. 3) continues its progression along arrow F2.

In a third step, the anti-adherent process liner 3 provided with the cross-linked adhesive silicone gel 2 passes in a corona treatment unit 14 in order to subject the layer of adhesive silicone gel 2, in particular its outer surface 2b (i.e., the surface opposite the process liner 3), to a corona treatment of a known type.

To that end, some technical precisions should be provided.

The silicone adhesive gel consists of a silicone polymer of the PDMS type, cross-linked and in gel form, and obtained from the chemical polyaddition reaction between polymethyl vinyl siloxanes and polymethyl hydrogen siloxanes in the presence of heat and a platinum-derived catalyst.

Unlike elastomer-type silicone, which has a high hardness, good elasticity, lower mobility of the chains and a naturally non-adhesive surface (the latter property is also particularly desired, used and appreciated in the relevant field), silicone in gel form has a very low hardness, a high viscosity, high mobility of the chains and significant adhesive properties.

More specifically, after physicochemical analysis, it has been shown that corona treated silicone gel undergoes the following modifications:
Creation of free radicals: $CH3 \rightarrow CH2$.
Surface oxidation and creation of polar groups such as hydroxyls and carbonyls.
Cleavage of the main skeleton of the PDMS-Si—O—Si chain.
The silicone goes from being hydrophobic to being hydrophilic.

In terms of surface properties, the chemical surface modifications experienced by the cross-linked silicone gel 2 during the corona treatment are reflected by an increase in the surface energy, evaluated through the measurement of the contact angle formed by a drop of water deposited on the surface of the material.

The applicant has thus noted that the innovative solution of applying corona treatment to the adhesive silicone gel makes it possible to generate a good adhesion on a polyurethane film, lastingly over time.

Once the corona treatment is done, a receiving substrate 4, for example a polyurethane film wound on a spool 15, is immediately coated onto the corona treated layer of the adhesive silicone gel 2 along arrows F3 for a so-called lining and calendaring operation.

Lastly, the assembly of three layers thus formed is wound on a spool 16 along arrow F4 for cutting and subsequent use, in particular after having removed the anti-adherent process liner 3 (see FIG. 4).

The innovation therefore makes it possible to generate strong and lasting adhesion of the corona treated adhesive silicone gel on various substrates that it would not be possible to obtain without treatment.

Indeed, after study, in particular of the holding power, it clearly appears that the traditional solution of corona treatment of the substrate used in the world of acrylic adhesives is ineffective in the case of a silicone adhesive gel, whereas the innovative solution of corona treatment of the silicone adhesive gel makes it possible to generate good adhesion on a polyurethane film, lastingly.

The method according to the present invention also makes it possible to make the surface of the corona treated silicone gel hydrophilic, and therefore to keep the adhesion between the treated gel and a hydrophilic substrate, even filled with water (see FIG. 11 and related description).

In fact, a second development step consisted of comparing the adhesion between the adhesive silicone gel and a hydrophilic polyurethane foam 5 mm thick, for different corona treatment options, monitoring the performance over time and when the film is filled with water. As in the case of adhesion on a polyurethane film, the innovative solution of subjecting the silicone adhesive gel to a corona treatment makes it possible to generate good adhesion on a polyurethane foam, lastingly. Furthermore, when the foam is filled with water, it remains perfectly adherent to the silicone gel.

The innovative method was applied to different types of materials in addition to the polyurethane films and foams already studied, and in particular:
- an expandable woven textile with a base of polyamide and polyurethane fibers not compatible with the cross-linking temperatures of the silicone gel due to the presence of the polyurethane fibers;
- a meltblown nonwoven textile with a base of thermofusible polyurethane not compatible with the cross-linking temperatures of the silicone gel;
- a stitchbond nonwoven textile with a base of polyester (PET) fibers, not compatible with the cross-linking temperatures of the silicone gel because they have a high thermal contraction and not compatible with direct coating due to its high porosity;
- a wetlaid nonwoven textile with a base of polyester (PET) synthetic fibers and natural cellulose fibers, compatible with the cross-linking temperatures of the silicone gel, but not compatible with direct coating due to its high porosity;
- an extruded thermofusible polyurethane film (for example, one of the faces of which is covered with an acrylic adhesive that is in turn protected by an anti-adherent liner.

For all of the materials produced, good stripping of the gel/substrate pair from the anti-adherent liner has been observed, as well as a good adhesive transfer capability from the liner to the substrate and good adhesion between the gel and the substrate.

Typically, the weight of the silicone adhesive gel transferred to the substrate is between 50 and 1000 g/m2, preferably between 50 and 300 g/m2 depending on the targeted level of adhesion on the patient's skin, defined by the final application.

Typically, the anti-adherent process liner compatible with the adhesive silicone gel is of the paper or PET type with a spread comprised between 30 and 300 g/m2, preferably between 40 and 150 g/m2, and having an anti-adherent coating compatible with the silicone adhesive in that the silicone can be coated onto this liner, cross-linked in contact therewith and next easily separated therefrom.

The layer of gel is deposited on the anti-adherent liner using the methods known in coating: scraper, transfer cylinder, extrusion through a flat die or cord deposition nozzles.

The layer of gel deposited on the liner is translucent, but it may also be dyed by pigments compatible with medical application and the reactive system of the silicone.

According to one alternative embodiment illustrated by FIG. 2, a semi-finished product, made up of an anti-adherent process liner 3, cross-linked adhesive silicone gel 2 and a protective liner 6, is provided from a spool 21.

In a first step, the protective liner 6 is removed (arrow F6) to be wound on a spool 22, while the cross-linked silicone gel/process liner assembly continues its movement along arrow F7.

In a second step, the cross-linked adhesive silicone gel 2 undergoes corona treatment via the corona treatment unit 14 so as to modify the structure of the outer face 2b of said silicone layer.

In a third step, a substrate 4 is unwound along arrow F8 from a spool 15 to coat the treated surface 2b of the adhesive silicone gel 2 immediately after said corona treatment so as to create a strong and lasting adhesion. The assembly of three layers (process liner, corona treated silicone gel and receiving substrate) continues to move along arrow F10 to be wound on an output spool 16 for cutting and subsequent use.

The result is identical to that of the method of FIG. 1. After having removed the anti-adherent process liner 3, the final adhesive material is as illustrated in FIG. 2, with the adhesive silicone surface 2a not having undergone the corona treatment being intended to come into contact with the skin of the patient to be treated.

Figure 5:
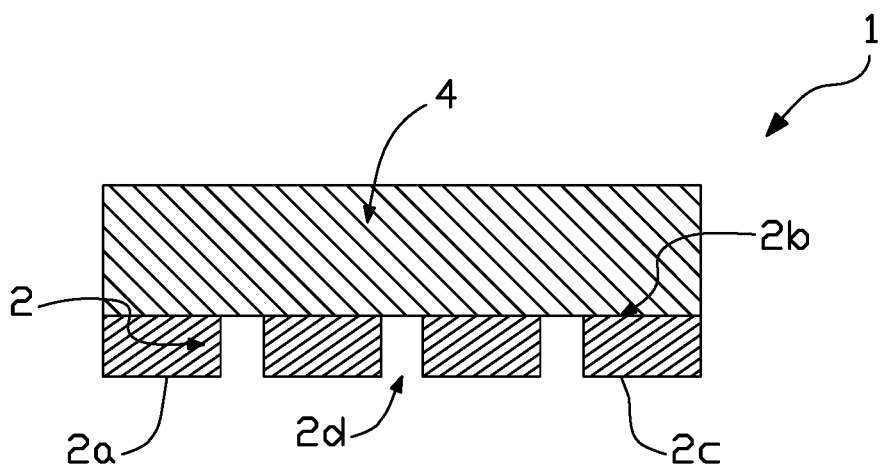
FIG. 5 is a sectional view of one alternative embodiment of FIG. 4.

As illustrated in FIG. 5, it is possible to coat the entire anti-adherent process liner 3 discontinuously so as to create an alternating pattern with zones provided with adhesive silicone gel 2c and zones 2d with no adhesive silicone gel. This solution allows the local creation of good steam breathability of the obtained complex material.

FIG. 6 shows a front view of the end result of such a method, with parallel patterns and strips.

Other patterns are possible, such as the crossed bands forming squares of FIG. 7, the crossed bands forming diamonds of FIG. 8, the discs of FIG. 9 or the crossed spirals of FIG. 10.

It is also possible to provide the adhesive silicone gel/receiving substrate complex with a compress 5, illustrated in FIG. 11. In this case, once the anti-adherent process liner 3 is removed, the surface 2a of the layer of adhesive silicone gel 2 is corona treated so as to modify the surface chemistry and the surface state of the gel prior to adhesion of the compress 5 so that the latter remains firmly bonded to said gel, even when wet and impregnated with secretions (for example, aqueous exudates from a wound).

Of course, the detailed description of the subject matter of the invention, provided solely as an illustration, is in no way limiting, technical equivalents also being comprised in the scope of the present invention.

Thus, various films can be used as receiving substrate, in particular polyethylene (PE), polypropylene (PP), polyamide (PA), copolyamide (Co PA), copolyester (Co PET), polyurethane (PU) or copolyurethane (Co PU).

Regarding nonwoven textiles, materials other than those previously cited can be used as receiving substrate: Cellulose, Viscose.

Regarding knit textiles, it is also possible to use acetate or acrylic in addition to all of the materials previously cited.

Lastly, regarding compresses, it is also possible to use the following materials, with or without an absorbing agent such as carboxymethylcellulose, hexa ethyl cellulose, sodium alginate or sodium polyacrylate, with or without a disinfectant or antimicrobial agent, and comprising or not comprising a web preventing adherence on the wound.

The invention claimed is:

1. A method for producing an adhesive material (1) for a medical application, comprising: providing an anti-adherent liner (3) with opposite first and second surfaces and a layer of an adhesive silicone gel (2) on the first surface of the anti-adherent liner (3), performing a corona treatment step to a surface (2b) of the adhesive silicone gel (2) that faces away from the anti-adherent liner (3) without performing a corona treatment step to the second surface of the anti-adherent liner, and coating the surface (2b) of the adhesive silicone gel (2) that had been subject to the corona treatment step onto a receiving substrate (4; 5).

2. The method of claim 1, further comprising cross-linking the silicone gel (2) before the corona treatment step.

3. The method of claim 2, wherein the step of coating the receiving substrate (4) with the adhesive silicone gel (2) is carried out in line with a step of coating the adhesive silicone gel (2) onto the anti-adherent liner (3).

4. The method of claim 2, wherein the step of coating the receiving substrate (4) with the adhesive silicone gel is carried out separately from a step of coating the adhesive silicone gel (2) onto the anti-adherent liner (3).

5. The method of claim 2, wherein the step for coating the receiving substrate (4) with the adhesive silicone gel (2) is performed by continuous solid surface coating.

6. The method of claim 2, wherein the adhesive silicone gel (2) coating is applied to the anti-adherent liner (3) discontinuously so as to generate localized zones (2d) with no gel.

7. The method of claim 1, wherein the receiving substrate (4) comprises a film of synthetic materials.

8. The method of claim 1, wherein the receiving substrate (4) comprises a woven or knit textile made from natural and/or synthetic fibers or fiber combinations.

9. The method of claim 1, wherein the receiving substrate (4) comprises a nonwoven textile made from natural and/or synthetic fibers or fiber combinations, obtained using a method applicable to its composition.

10. The method of claim 1, wherein the receiving substrate (5) comprises a water-absorbent or draining foam serving to absorb or drain the exudates of a wound.

11. The method of claim 1, wherein the receiving substrate (4) comprises a mechanical damping foam serving to protect against impacts, pressure and/or friction.

12. The method of claim 1, wherein the receiving substrate (4) comprises a three-dimensional knit textile from natural and/or synthetic fibers or fiber combinations, having mechanical damping properties to protect against impacts, pressure and/or friction.

13. The method of claim 1, wherein the receiving substrate (4) is associated with different functional layers and/or includes water absorption agents, disinfecting agents or other functional additives.

14. The method of claim 1, wherein the adhesive silicone gel (2) is dyed using pigments compatible with the anticipated medical application and the composition of said adhesive silicone gel.

15. An adhesive material for medical applications (1) obtained using the method of claim 1, wherein the silicone layer is a cross-linked silicone gel (2) having undergone a corona treatment on the surface (2a, 2b) intended to coat the receiving substrate.

* * * * *